United States Patent [19]

Milosavljevic

[11] Patent Number: 6,001,562

[45] Date of Patent: Dec. 14, 1999

[54] DNA SEQUENCE SIMILARITY RECOGNITION BY HYBRIDIZATION TO SHORT OLIGOMERS

[75] Inventor: Aleksandar Milosavljevic, Westmont, Ill.

[73] Assignee: The University of Chicago, Argonne, Ill.

[21] Appl. No.: 08/438,506

[22] Filed: May 10, 1995

[51] Int. Cl.$^6$ .............................. C12Q 1/68; C07H 21/02; C07H 21/04

[52] U.S. Cl. .............................. 435/6; 536/23.1; 536/24.3

[58] Field of Search .................................. 435/6; 935/77, 935/78; 536/23.1, 24.3

[56] References Cited

U.S. PATENT DOCUMENTS 5,202,231  4/1993  Drmanac et al. ........................... 435/6

FOREIGN PATENT DOCUMENTS 0 373 203 B1  8/1994  European Pat. Off. .......... C12Q 1/68

OTHER PUBLICATIONS

Drmanac et al. Electrophoresis 13: 566–573 (1992).

Drmanac et al. The First Int'l Conf. on Electrophoresis, Superconductors and Human Genetics, Proceedings of the Apr. 10–13, 1990 Conf. at FL St Univ. Tallahassee, FL.

Yura et al. Nucleic Acids Research 20(13):3305–3308 (1992).

Milosavljevic et al., Abstract from Proc. of the Second Int'l Workshop on Sequencing by Hybridization, Houston, TX, Oct. 30, 1993.

Drmanac, R., et al., "Partial Sequencing by Oligo–Hybridization: Concept and Applications in Genome Analysis", The First International Conference on Electrophoresis, Supercomputing and the Human Genome, Proceedings of the Apr. 10–13, 1990 Conference at Florida State University, Tallahassee, FL.

Hide, Winston, et al., "Biological Evaluation of $D^2$, an Algorithm for High–Performance Sequence Comparison," *J. of Computational Biology*, 1(3):199–215, 1994.

Lennon, Gregory G., et al., *Perspectives, Trends in Genetics,* "Hybridization analyses of arrayed cDNA libraries," *Trends in Genetics* 7(10):314–317, Oct. 1991.

Milosavljevic, Aleksandar, et al., "Information for Massive Hybridization Experiments," Abstract from Proc of the Second Int'l. Workshop on Sequencing by Hybridization, Houston, TX, Oct. 30, 1993.

Milosavljevic, Aleksandr, "Macromolecular sequence analysis via algorithmic mutual information," Abstract, ML/COLT'94 Workshop on Applications of Descriptional Complexity to Inductive, Statistical, and Visual Inference, Jul. 10, 1994.

Milosavljevic, Aleksandar, "Discovering Sequence Similarity by the Algorithmic Significance Method," Proceedings of the First International Conference on Intelligent Systems for Molecular Biology, AAAI Press, Menlo Park, California, pp. 284–291, 1993.

Milosavljevic, Aleksandar, et al., "Discovering simple DNA sequences by the algorithmic significance method," *CABIOS*, 9(4):407–411, 1993.

Pevzner, Pavel A., "Statistical distance between texts and filtration methods in sequence comparison," *CABIOS*, 8(2):121–127, 1992.

Pevzner, Pavel A., "1–Tuple DNA Sequencing: Computer Analysis," *J. of Biomolecular Structure & Dynamics*, 7(1):063–073, 1989.

Privara, Igor, et al., "Mathematical Foundations of Computer Science 1994," 19th Int'l Symposium MFCS '94, Kosice, Slovakia, Aug. 1994.

*Primary Examiner*—W. Gary Jones
*Assistant Examiner*—Ethan Whisenant
*Attorney, Agent, or Firm*—Arnold, White & Durkee

[57] ABSTRACT

Methods are disclosed for the comparison of nucleic acid sequences. Data is generated by hybridizing sets of oligomers with target nucleic acids. The data thus generated is manipulated simultaneously with respect to both (i) matching between oligomers and (ii) matching between oligomers and putative reference sequences available in databases. Using data compression methods to manipulate this mutual information, sequences for the target can be constructed.

15 Claims, 5 Drawing Sheets

| | | | | | | | |
|---|---|---|---|---|---|---|---|
| 1 | AAGGTTG | 29 | CATTGCG | 57 | GAGGAGG | 85 | TCCTCCA |
| 2 | AATCACG | 30 | CCACGGC | 58 | GAGGCTG | 86 | TGAAGCT |
| 3 | ACCTGCA | 31 | CCACGGG | 59 | GAGTGCA | 87 | TGATCAG |
| 4 | ACCTGGA | 32 | CCAGGCT | 60 | GATTTTC | 88 | TGATGGT |
| 5 | ACTGTTC | 33 | CCCACGG | 61 | GCAAATC | 89 | TGCAGTG |
| 6 | AGAAGGT | 34 | CCCCCCC | 62 | GCCCACG | 90 | TGCCGCC |
| 7 | AGCAGCT | 35 | CCCGTGC | 63 | GCCGCCC | 91 | TGCTGGA |
| 8 | AGCGCAA | 36 | CCGCCTG | 64 | GCCTGGA | 92 | TGCTGGG |
| 9 | AGCTACT | 37 | CCTGCGC | 65 | GCGGCTG | 93 | TGGACAA |
| 10 | AGCTGAC | 38 | CGAGCAT | 66 | GCGTCAA | 94 | TGGACCT |
| 11 | AGCTGCA | 39 | CGCCCAC | 67 | GGACAAG | 95 | TGGAGCA |
| 12 | AGGAGTTC | 40 | CGGGTGA | 68 | GGACATC | 96 | TGGAGGA |
| 13 | AGGATCG | 41 | CGTGGCC | 69 | GGAGAAG | 97 | TGGATGA |
| 14 | AGTGGAC | 42 | CTACAGC | 70 | GGAGATG | 98 | TGGATTT |
| 15 | ATGAAGC | 43 | CTCACCA | 71 | GGATGAA | 99 | TGGGATA |
| 16 | ATGCGAC | 44 | CTGACCA | 72 | GGATGAG | 100 | TGGGATC |
| 17 | ATGCTCC | 45 | CTGATGA | 73 | GGCGGCG | 101 | TGGGATG |
| 18 | ATTGACC | 46 | CTGCGCA | 74 | GGTGAAG | 102 | TGGGATT |
| 19 | ATTTFCC | 47 | CTGGATT | 75 | GGTGATG | 103 | TGGTGAT |
| 20 | CAAGAAG | 48 | CTGGCCT | 76 | GTGAGCC | 104 | TGGTGGA |
| 21 | CAAGGAG | 49 | CTGGGAT | 77 | GTGCCGC | 105 | TGTGGAC |
| 22 | CACAGTT | 50 | CTGGGATC | 78 | GTGCTGA | 106 | TGTGTGC |
| 23 | CACCAAC | 51 | GAAATCG | 79 | TACGACG | 107 | TTCCAGG |
| 24 | CACCAAG | 52 | GAAGAAG | 80 | TATCCCC | 108 | TTGGTCA |
| 25 | CAGAAGT | 53 | GAATCGC | 81 | TATCGGC | 109 | TTTFCCA |
| 26 | CAGCTGG | 54 | GACATCG | 82 | TATGACC | | |
| 27 | CATCCCA | 55 | GAGCCTC | 83 | TCCCAGC | | |
| 28 | CATGGTGC | 56 | GAGCGTG | 84 | TCCGTCA | | |

FIG. 2

| | | | |
|---|---|---|---|
| 1<br>AATCAC-G | 15<br>TCAGCAC | 29<br>G-C-G-A-T-T-C | 43<br>G-AACAGT |
| 2<br>C-GTGATT | 16<br>GTGCTGA | 30<br>G-A-A-T-C-G-C | 44<br>ACTGTT-C |
| 3<br>ATTTTCC | 17<br>TGCTGGG | 31<br>G-CACCATG | 45<br>GGATGA-G |
| 4<br>G-GAAAAT | 18<br>C-C-C-A-G-C-A | 32<br>CATGGT-G-C | 46<br>CTCATC-C |
| 5<br>CATTGC-G | 19<br>T-G-C-T-C-C-A | 33<br>T-T-G-A-C-G-C | 47<br>A-G-G-A-T-C-G |
| 6<br>C-GCAATG | 20<br>GGATGAA | 34<br>G-CGTCAA | 48<br>C-G-A-T-C-C-T |
| 7<br>TGCAGG-T | 21<br>T-T-C-A-T-C-C | 35<br>TCATCA-G | 49<br>C-C-C-A-C-G-G |
| 8<br>A-C-C-T-G-C-A | 22<br>TGGAGCA | 36<br>C-T-G-A-T-G-A | 50<br>T-A-T-C-C-C-A |
| 9<br>CAGCTGG | 23<br>GATTTF-C | 37<br>T-GGAGGA | 51<br>C-C-G-T-G-G-G |
| 10<br>C-T-G-G-G-A-T-C | 24<br>GAAAAT-C | 38<br>T-C-C-T-C-C-A | 52<br>T-G-G-G-A-T-A |
| 11<br>G-A-TCCCAG | 25<br>T-G-G-G-A-T-C | 39<br>C-AACCTT | 53<br>G-CGGCTG |
| 12<br>CCAGCTG | 26<br>G-A-T-C-C-C-A | 40<br>A-A-G-G-T-T-G | 54<br>C-A-G-C-C-G-C |
| 13<br>AGGAGTT-C | 27<br>C-A-G-A-A-G-T | 41<br>TTTTCCA | 55<br>A-G-C-T-G-C-T |
| 14<br>G-AACTCC-T | 28<br>ACTTCTG | 42<br>T-G-G-A-A-A-A | 56<br>AGCAGCT |

FIG. 3

DNA SEQUENCE SIMILARITY RECOGNITION BY HYBRIDIZATION TO SHORT OLIGOMERS

The government may own certain rights in the present invention pursuant to grants from the W-31-109-ENG-38 from the Department of Energy.

FIELD OF THE INVENTION

The invention relates to methods of determining sequence similarities between known and unknown nucleic acids. In a particular embodiment, the invention concerns methods for determining a nucleic acid sequence using hybridization experiments and a computer-assisted comparison of the hybridization results.

BACKGROUND OF THE INVENTION

Comparison of nucleic acids at the molecular level currently is based on three general types of sequence comparisons: (i) "wet" comparisons where nucleic acid probe fragments are hybridized to target nucleic acids under varying degrees of stringency; (ii) "dry" comparisons where a fragment having a known sequence is compared via computer against a database containing known sequences; and (iii) "restriction fingerprint" comparisons where a DNA fragment is cut by restriction endonucleases to obtain a specific set of fragments whose lengths are compared against other sets of cleaved fragments obtained experimentally or computed from known sequences.

A fourth kind of comparison, generally referred to as "hybridization fingerprinting," is performed by hybridizing a set of short oligomer probes with a target DNA fragment, identifying complementary oligomers that occur within the fragment. Two versions of this approach have been proposed. The first method counts common occurrences of oligomers in the fragment and in a candidate matching sequence (Lennon and Lehrach, 1991; Drmanac et al., 1991). The second method is based on oligomer overlaps and a comparison of the reconstructed sequence against a candidate matching sequence (Drmanac et al., 1991). The first method, by design, ignores shared subwords (overlaps) between the oligomers, while the second method utilizes shared subwords for the purpose of sequence reconstruction, which is an intermediate step in the recognition of similarity.

In contrast to gel-based sequencing and restriction analysis, which are essentially one-dimensional separation experiments, hybridization experiments do not require one-dimensional separation and thus can be economically conducted on a much larger scale by utilizing high-density two-dimensional arrays of immobilized DNA fragments (Format 1 hybridization experiments) or oligomer probes (Format 2 experiments). This enhances the opportunity to automate the process and, therefore, increase the amount of information generated within a given time period. Furthermore, automation can lead to increased cost efficiency. For example, data collection throughput of several million probe/target hybridization scores per day can be achieved in a laboratory of small size by utilizing current hybridization technology (Drmanac et al., 1994a; Drmanac et al., 1993).

An example of hybridization-based technology is provided in U.S. Pat. No. 5,202,231. There, a method is described for sequencing based on hybridization of sets oligonucleotide probes and compilation of overlapping, completely complementary probes to generate a sequence. The shortcoming of this approach is that the initial reliance on overlap may introduce significant error into the sequence. While providing a simple and potentially automated procedure, this method is unsatisfactory in terms of accuracy and confidence. Thus, there remains a need for more sophisticated, hybridization-based techniques for the comparison of nucleic acids.

SUMMARY OF THE INVENTION

In addressing the limitations in the prior art, it is an objective of the present invention to provide a hybridization-based method for sequence comparison that overcomes the limitations in the prior art. The proposed method simultaneously considers both shared subwords of identified oligomer probes and the structure of candidate matching sequences. An important aspect of this method is that it utilizes oligomer lists directly following identification of matching oligomers, avoiding sequence reconstruction as an intermediate step.

In satisfying these objectives, there is provided a method for detecting sequence similarity between at least two nucleic acids, comprising the steps of (a) identifying a plurality of putative subsequences from a first nucleic acid; (b) comparing the subsequences with at least a second nucleic acid sequence. In another embodiment of the foregoing, the method further comprises the step of (c) aligning the subsequences using the second nucleic acid sequence in order to maximize (i) matching between the subsequences and the second nucleic acid sequence and (ii) mutual overlap between the subsequences, whereby the alignment predicts the sequence of the first nucleic acid.

In yet another embodiment, the foregoing method is applied wherein the plurality of subsequences is identified by hybridization of the first nucleic acid with a set of oligonucleotide probes. In one embodiment, this is achieved by (a) simultaneously contacting the first nucleic acid with an array of the set of oligonucleotide probes under conditions permitting hybridization of the oligonucleotide probes to substantially complementary regions within the first nucleic acid molecule; and (b) determining hybridization of individual oligonucleotide probes.

In an alternative embodiment of the foregoing, the plurality of subsequences is identified by (a) simultaneously contacting the first nucleic acid, arrayed as a collection of nucleic acid fragments, with individual oligonucleotide probes of the set of oligonucleotide probes under conditions permitting hybridization of the set of oligonucleotide probes to substantially complementary regions within the arrayed collection of nucleic acid fragments; and (b) determining hybridizations of the oligonucleotide probes with the individual nucleic acids.

In yet another alternative embodiment, the plurality of subsequences is identified by (a) contacting the first nucleic acid with an array of the set of oligonucleotide probes and a second set of oligonucleotide probes under conditions permitting hybridization of the oligonucleotide probes to regions within the first nucleic acid molecule that are substantially complementary to concatenations of the oligonucleotide probes; and (b) determining hybridization of the oligonucleotide probes.

In still yet another embodiment according to the foregoing, the putative subsequences are from six to twenty nucleotides. In even yet another embodiment, the second nucleic acid is predicted from an amino acid sequence or motif.

In still yet a further embodiment, the subsequences are used as a query to search a collection of nucleic acid sequences. Alternatively, the second nucleic acid is used as a query to search a collection of nucleic acid sequences, each nucleic acid sequence of the collection being represented by a list of subsequences.

The preceding methods may be practiced such that the alignment score is a function of encoding length of the second nucleic acid where the subsequences are a source dictionary for data compression. Alternatively, the alignment score is a function of encoding length of said subsequences where said second nucleic acid is a source dictionary for data compression.

Alignment, according to the present invention, is based on an estimate of mutual information between said second sequence and the said subsequences or on an estimate of mutual information between said second sequence and the said subsequences. The significance of similarity, having been determined by either of the foregoing methods, can be determined using basic or extended significance methods.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 2: Oligomers used in hybridization experiments.

FIG. 3: The list of 56 oligomers in the source list $s=C'_5$ for $C_5$. The oligomers are listed in the decreasing order of their hybridization intensities. The 6-mer and 7-mer subwords that also occur in $C_5$ are not interrupted by dashes—a total of 33 oligomers contain a 6-mer from $C_5$, including the 13 of them that contain a 7-mer. Note that the highest coincidence with the sequence occurs at the top of the list, as expected. There are a total of 23 oligomers that do not share a 6-mer with the true sequence. Some of them occur in reverse orientation while the others represent false positives.

DETAILED DESCRIPTION OF THE INVENTION

Figure 1:
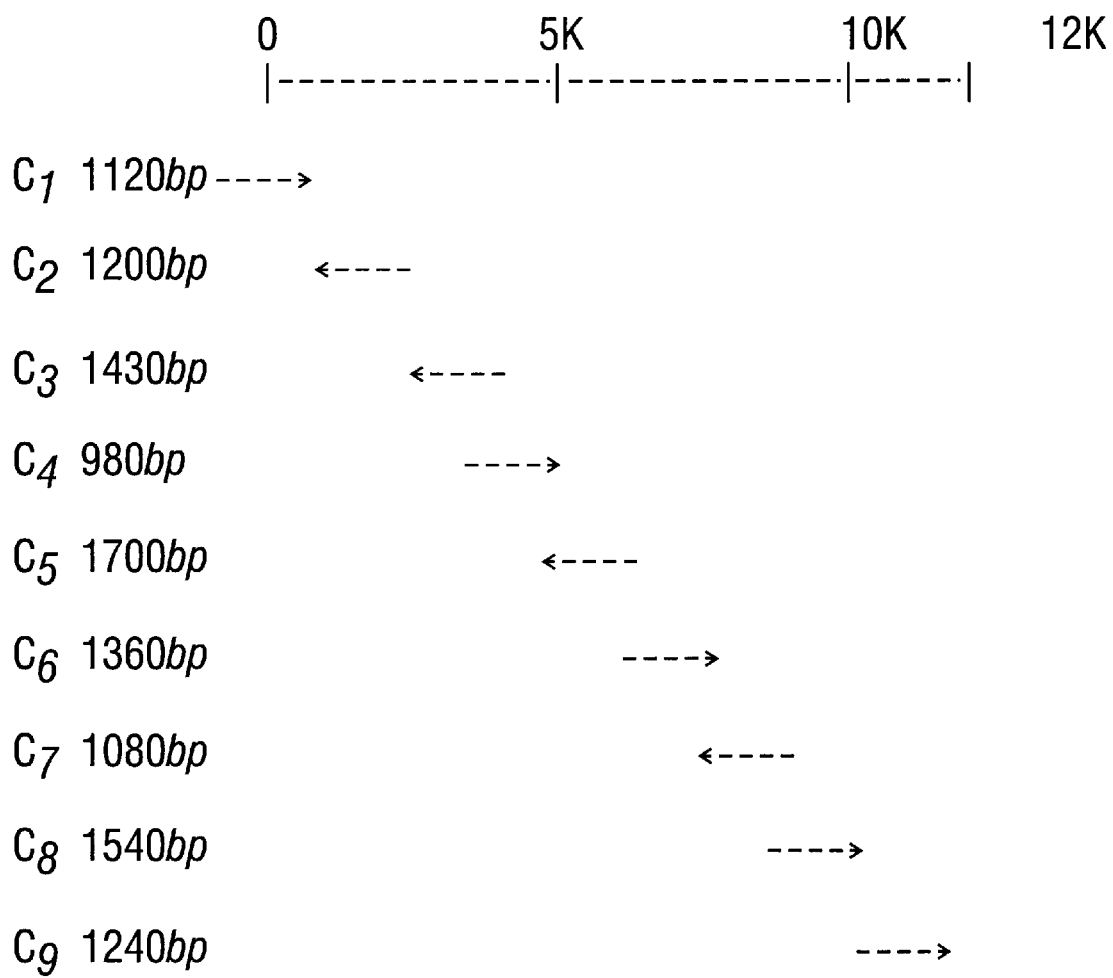
FIG. 1: Clones from a human genomic DNA region of the dystrophin gene.

There is proposed here a variation of the "hybridization fingerprint" method for comparison of nucleic acids. An information-theoretic proof has been used to validate the method and demonstrate superior performance in terms of specificity of recognition. There also is demonstrated an efficient computational parameters for optimal sequence reconstruction.

There are numerous scenarios where the present method can be applied. For example, a known sequence or a sequence pattern can be used as a query for a database of oligomers, the oligomers having been compiled for a large number of clones covering a significant portion of one or several genomes. Alternatively, the oligomers may be based on clones from cDNA libraries, in which case they represent a significant portion of expressed genes in a particular type of cells.

In the case of genomic libraries, the recognition procedure can be used to guide sequencing of genomic regions. For example, the recognition information can be used to bridge gaps between sequenced regions, a laborious step in large-scale genomic sequencing. This is accomplished by using a redundant collection of overlapping clones that covers a particular genomic region. The clones are probed by hybridization to short oligomers in order to determine hybridization signatures and oligomer lists for each clone. The oligomer lists can be used to "anchor" the clones by recognizing their cognate sequence within particular regions. The hybridization signatures are then used to find a "bridge" between the anchored clones consisting of a set of overlapping clones. The overlapping clones can then be sequenced in order to close the gap between the two known regions.

In the case of cDNA libraries, complete sets of cDNA clones that come from one or more cell types or from a number of organisms may be queried. In addition, an oligomer list for a particular clone may be used as a query for a database of known DNA sequences or motifs. If a sequence that is highly similar to that of the clone is already present in the database, it will be recognized by this method. This method will gain in importance as the amount of sequenced DNA grows. Instead of being resequenced, most of the clones of interest will simply be recognized by this method and unnecessary sequencing will be avoided.

In addition to comparing oligomer lists against DNA sequences, the method can easily be applied to comparisons against amino acid sequences and DNA sequence patterns. The most straightforward application of this approach would be to represent an amino acid sequence or a DNA sequence pattern, implicitly or explicitly, by a set of DNA sequences, and then to compare such sequences against oligomer lists for a large number of clones. This will enable rapid identification of genes that encode particular short amino acid sequences or that contain a particular DNA sequence motif. Identification of genes that encode a particular amino acid sequence currently is a tedious step in gene hunting endeavor. The present method, especially if coupled with an adequate short oligomer selection strategy, will improve efficiency of this process by orders of magnitude.

An additional application of the present invention would involve the use of certain information, available a priori, concerning the target nucleic acid. For example, one may know a priori that the target nucleic acid resembles one of a limited number of possible sequences or a family of sequences. The comparison can be applied to the target, further taking into account the established relationship with other sequences.

A. Hybridization Methods

The hybridization techniques that are necessary for obtaining hybridization fingerprints can be of virtually any kind: clones-down (Format 1, "classic"), probes-down (Format 2, "sequencing chip") or any combinatorial extension thereof (Format 3). While all the formats give the same kind of information (correspondence with oligomers) and are interpreted the same way, the convenience of using a particular format depends on the number and size of clones and probes to be hybridized.

In Format 1, nucleic acids of unknown sequence, generally of about 100–10,000 nucleotides in length, are arrayed on a solid support or filter so that the unknown samples themselves are immobilized (Strezoska et al., 1991; Drmanac & Crkvenjakov, U.S. Pat. No. 5,202,231). Replicas of the array are then interrogated by hybridization with sets of labeled probes of about 6 to 10 residues in length.

In the "probes-down" Format 2, a sequencing chip is formed from an array of a set of oligonucleotides with known sequences of about 6 to 10 residues in length (Southern, WO 89/10977; Khrapko et al., 1991; Southern et al., 1992). The nucleic acids (100–10,000 bp) of unknown sequence are then labeled and allowed to hybridize to the immobilized oligonucleotides.

Format 3 combines certain features from both of the earlier techniques. In Format 3, as described by (Drmanac, 1994), nucleic acid sequences are determined by hybridization with two sets of oligonucleotide probes of known sequences. An original set of probes is arrayed on a sequencing chip, the nucleic acids of unknown sequence are allowed to hybridize, and then the hybridized complexes are themselves interrogated by hybridization with another set of labeled probes. The method achieves a larger effective length of a probe (beyond 10 base pairs), thus allowing analysis of fragments longer than 10,000 nucleotides.

For the purposes of this application, a "set" of oligonucleotides or nucleic acids is defined as one or more oligonucleotides or nucleic acids. An "array" of oligonucleotides or nucleic acids entails the presentation of a set in a two-dimensional, discernable pattern in which the location of a particular oligonucleotide or nucleic acid is identifiable.

B. Scoring Function

In order to compare a particular oligomer list against a particular target sequence, a scoring function must be designed. The scoring function of the present method can be any of a class of scoring functions that combine the following two features. First, the scoring function utilizes oligomer overlaps (two oligomers that significantly overlap contribute more toward a score). Second, an overlap of oligomers contributes to a score only if it also occurs in the candidate matching sequence.

Thus, the method attempts to construct contiguous stretches of overlapping oligomers that best match the contiguous stretches in the candidate matching sequence, ignoring overlaps that do not resemble the sequence. The final score depends on the degree of achieved resemblance. Variants of this method can also utilize imperfect overlaps, i.e., situations where two oligomers only share subwords, as opposed to overlaps. The combination of the two features has not been utilized in related methods (Lennon and Lehrach, 1991; Drmanac et al., 1991).

A method that is based on counting co-occurrences of oligomers on the list and in the candidate matching sequence has been proposed before (Lennon and Lehrach, 1991). A scoring function for such methods does not utilize the first feature discussed above, thus leading to suboptimal performance. In fact, there are numerous DNA sequence comparison methods (Hide et al., 1994; Pietrokovski et al., 1990; Pizzi et al., 1991; Blaisdell, 1986; Quentin, 1994; Pearson and Lipman, 1988) that utilize various scoring functions. Because of their speed, such methods are used for preliminary screening of sequences (Pevzner, 1992). The candidate sequences that pass the screening step are then compared by more rigorous, but also more time-demanding methods. Such methods may be viewed as the opposite of the present method, as the oligomer sequences are broken into subwords for the purpose of comparison. In the present method, the entire set of oligomers is implicitly treated as a sequence.

The first two steps of the recognition method are basically the same as the first two steps in sequencing by hybridization (Drmanac and Crkvenjakov, U.S. Pat. No. 5,202,231). Clones that are few hundred to few thousand bases long are hybridized with oligomer probes of short length under conditions that enable approximate discrimination of oligomer probes whose complement is present or absent in the sequence of the clone. The recognition method can tolerate much more error than the sequencing method because the sequencing method utilizes oligomer overlaps exclusively, while the recognition method takes advantage of any shared subword of sufficient length. The end-mismatch error, which is most frequent in hybridization experiments, is likely to destroy oligomer overlaps and thus impede sequence reconstruction. Long shared subwords that are necessary for recognition, however, will remain. The key to the vitality of the recognition method lies in the fact that it utilizes information that is present in the putative matching sequence—information that is not used for sequencing by hybridization (Drmanac and Crkvenjakov, U.S. Pat. No. 5,202,231).

A hypothetical example illustrates why the present method is an advance over previous methods that include sequencing by hybridization as an intermediate step. Sequencing by hybridization is illustrated below. A sequence of twenty is reconstructed by identifying the thirteen 8-mers that are contained therein:

| | |
|---|---|
| 1 | GAAGTTGC |
| 2 | AAGTTGCG |
| 3 | AGTTGCGC |
| 4 | GTTGCGCA |
| 5 | TTGCGCAT |
| 6 | TGCGCATG |
| 7 | GCGCATGC |
| 8 | CGCATGCA |
| 9 | GCATGCAC |
| 10 | CATGCACA |
| 11 | ATGCACAA |
| 12 | TGCACAAG |
| 13 | GCACAAGT | sequence: GAAGTTGCGCATGCACAAGT (SEQ ID NO:1)

One problem with sequencing by hybridization is the requirement that all possible oligomers of certain length be hybridized. Thus, sequencing of a few kilobases of unknown DNA requires hybridizations with all possible 65,536 8-mers or with all possible 16,384 7-mers. The total number of hybridizations can, in principle, be reduced as long as the overlaps are sufficient to reconstruct the sequence, as illustrated below:

| | |
|---|---|
| 1 | GAAGTTGC |
| 5 | TTGCGCAT |
| 9 | GCATGCAC |
| 13 | GCACAAGT | sequence: GAAGTTGCGCATGCACAAGT (SEQ ID NO:1)

Note that instead of the total set of thirteen oligomers in the first example, now only four are used. This indicates that only a fraction of the possible oligomers may suffice in some cases. The sequence is now computed as the shortest sequence that contains within it occurrences of all four oligomers. An efficient computational method that optimally reconstructs the sequence by this method is unlikely to exist (Garey and Johnson, 1979) and, therefore, approximate methods must be applied in practice.

Due to the inaccuracy of hybridization experiments, in practice the oligomers are identified only within certain degree of error. Hybridization error most frequently results in one-base mismatches at the ends of oligomers, but may affect internal bases as well. The presence of error further complicates the reconstruction problem, i.e., it is necessary to reconstruct sequence by simultaneously minimizing the sequence length and the number of postulated hybridization errors.

An example of an optimal sequence reconstruction in the presence of error is show below. The reconstructed sequence is of minimal length when the number of hybridization errors (denoted by '?') is restricted to at most two:

```
13          CCACAAGT
 1            GAAGTTGC
 5              *  TTGCGCAT
 9                    GTATGCAC
``` sequence: CCA?AAGTTGCG?ATGCAC (SEQ ID NO:2)

In this scenario, mismatches in the first base of oligomer 13 and the second base of oligomer 9 are introduced. The mismatches have resulted in a new sequence that is obtained by moving oligomer 13 from the last to the first position. In addition to the scrambling of the true sequence, the errors have resulted in two bases being rendered ambiguous (denoted by '?').

If such erroneously reconstructed sequences (even partially reconstructed) were used as queries in similarity searches, it might not be possible to identify matching sequences even if they existed in the database. If lists of oligomers were used directly, without committing them a priori to any particular sequential arrangement, the error might be avoided and the correct match would be more likely to be found. An illustration of the advantage of this approach is provided below:

plete and noisy data (practical solutions employ approximations), linear-time analysis is proposed for efficient sequence recognition, thus allowing exhaustive searching of sequence databases. Thus, if the goal is sequence comparison, using the list of oligomers as a query instead of using an intermediate step of sequence reconstruction will be advantageous. As the amount of sequenced DNA available in databases grows, more and more sequences will be recognized using this method rather by sequencing de novo.

The recognition method may be particularly useful in the situation where the set of possible sequences for the target sequence is known a priori. In that case, the highest scoring sequence from the set would be recognized as identical to the sequence of the examined nucleic acid. The scoring function also may incorporate the a priori probability of individual matches.

In the following, a particular implementation of the recognition method is provided. While there are many possible implementations and scoring functions within the general method, there is an outstanding class of scoring functions which can be proven to be information-theoretically superior to methods that involves sequencing as an intermediate step.

In contrast to sequencing by hybridization (Drmanac and Crkvenjakov, U.S. Pat. No. 5,202,231), which aims to determine sequence information based on oligomer overlaps, the recognition method determines how well a particular known sequence matches up with a given set of oligomers. For that purpose, a scoring function will be used that measures the amount of information (in bits) revealed about a candidate matching sequence by an oligomer set. The amount of information is measured by the length (in bits) of the most concise description (encoding) of how a candidate matching sequence can be assembled from a given oligomer list.

C. Recognition by Minimal Length Encoding

There are many possible ways to describe (encode) a given sequence using a list of oligomers, or, vice versa, to encode a list of oligomers using a given sequence. A particular method is used here that is an extension of the basic macro substitution data compression scheme (Storer, 1988). Other generally applicable methods include dictionary-based compression schemes and their parallel implementations (Storer, 1988), statistical model-based compression schemes (Bell et al., 1990), adaptive and pre-

```
13    CCACAAGT                    1     GAAGTTGC
 1      GAAGTTGC                  5       TTGCGCAT
 5        *  TTGCGCAT             9         GTATGCAC
 9              GTATGCAC         13            CCACAAGT (SEQ ID NO:2)                                           (SEQ ID NO:3)
        CCA?AAGTTGCG?ATGCAC              GAAGTTGCG?AT?CACAAGT
        |||||||| ||||||                  ||||||||| || ||||||
sequence:   GAAGTTGCGCATGCACAAGT         GAAGTTGCGCATGCACAAGT
(SEQ ID NO:1)                                           (SEQ ID NO:1)
```

Using a scoring function based on the number of matching nucleotides, the optimally reconstructed sequence (left) achieves score 14 while the recognition score (right) is 18, due to the fact that oligomers are assembled so that they most resemble the candidate sequence. In fact, by applying a more sophisticated comparison method and by utilizing the information in the candidate matching sequence, it is possible to completely eliminate the small amount of mismatch error that is present in the oligomer set.

In contrast to the optimal sequence reconstruction problem, which is computationally intractable for incomdictive compression schemes (Williams, 1991), and other approaches that have been proposed in the field of data compression. Generally, a compression algorithm needs to be adapted in order to take advantage of oligomer overlaps. In the following examples, there is presented a basic macro substitution compression scheme, which is extended slightly to utilize possible oligomer overlaps.

First, let $I_{Ao}(t)$ denote the encoding length of sequence t by itself and let $I_{Ao}(t/s)$ denote the encoding of target sequence t relative to a source s. The source can either be a list of oligomers or a reconstructed sequence; the latter may be specifically denoted by s'. Subscripts $A_o$ and A denote decoding methods that define coding schemes.

When encoding a sequence by itself, a repeated occurrence of a word is replaced by a pointer to its previous occurrence within the same sequence. One must assume that a pointer consists of two positive integers—the first integer indicates the beginning position of a previous occurrence of the word while the second integer indicates the length of the word. For example, the sequence AGTCAGTTTT (SEQ ID NO:4) may be encoded as AGTC (1,3) (7,3) where (1,3) points to the occurrence of AGT from position 1 to position 3, and (7,3) points to the occurrence of TTT from position 7 to position 9 in the original sequence.

The decoding method $A_o$ comprises the following two steps. First, replace each pointer by a sequence of pointers to individual letters and, second, replace the new pointers by their targets in the left-to-right order. Continuing the example, the first step would yield AGTC (1,1)(2,1)(3,1)(7,1)(8,1)(9,1), and the second step would yield the original sequence. From this decoding approach, it should be obvious that the original sequence can be obtained despite overlaps of pointers and their targets, as is the case with the pointer (7,3) in the example.

When encoding a target sequence relative to a source sequence, the pointers point to the occurrences of the same words in the source. Consider an example where the target sequence is GATTACCGATGAGCTAAT (SEQ ID NO:5) and the source sequence is ATTACATGAGCATAAT (SEQ ID NO:6). The occurrences of some words in the target may be replaced by pointers indicating the beginning and the length of the occurrences of the same words in the source, for example, G(1,4)CCG(6,6)(13,4). The decoding method A is very simple—it only needs to replace pointers by words.

In either kind of encoding, one can think of the encoded sequence as being parsed into words that are replaced by pointers and into the letters that do not belong to such words. one may then represent the encoding of a sequence by inserting dashes to indicate the parsing. In the self-encoding example, the parsing is A-G-T-C-AGT-TTT, while in the relative-encoding example the parsing is G-ATTA-C-C-G-ATGAGC-TAAT.

Next, the problem of encoding a target sequence relative to a list of oligomers is addressed. A pointer now consists of three numbers: an index of an oligomer, the beginning position within the oligomer and the length. It is important to note that the length can exceed the length of an individual oligomer, provided a unique continuation can be found based on the oligomer suffix. To illustrate this point, return to the example given above:

| 1  | GAAGTTGC |
| 5  | TTGCGCAT |
| 9  | GTATGCAC |
| 13 | CCACAAGT |

In the new coding scheme, the true sequence can be encoded relative to the four oligomers above by a single pointer (1,1,20).

An important feature of the new decoding method is that it can recognize unique continuations of an oligomer by finding its longest suffix that has a unique additional occurrence, but not as a suffix of another oligomer. The additional occurrence of the suffix (possibly within the same oligomer) defines a continuation. More precisely, if the length recorded in a pointer exceeds the oligomer length, the decoding algorithm breaks down the pointer into two new pointers. The first new pointer is the same as the original pointer with the length decreased so as not to exceed the length of the oligomer. The second new pointer points to the oligomer that contains an occurrence of the longest suffix of the original oligomer; it is required that the occurrence be unique and not be a suffix. This procedure is repeated as long as there are pointers that point beyond an oligomer.

In the preceding example, the suffix TTGC of oligomer 1 points to oligomer 5, resulting in the pointer being broken down into (1,1,8)(5,5,12). After repeating the procedure two more times using the suffixes AT and CAC, the following list of pointers that point within individual oligomers is produced:

(1,1,8)(5,5,4)(9,5,4)(13,5,4)

The next step in the decoding method is a simple replacement of pointers by targets, as described before, yielding the correct target sequence:

GAAGTTGCGCATGCACAAGT (SEQ ID NO:1)

It is important to note that this decoding scheme implicitly takes advantage of the fact that oligomers may share subwords. Overlaps between oligomers need not be exact, as they are obviously not in case of oligomers 5 and 9 (mismatch in the second position of oligomer 9), and 9 and 13 (mismatch in the first position of oligomer 13). Hybridization errors do not interfere as long as the subword structure of oligomers provides enough information about continuations. Indeed, the correct target sequence would be encoded by the same single pointer even in the absence of hybridization errors. This stands in sharp contrast to sequence reconstruction, where identical errors lead to a scrambled and incomplete reconstruction, as demonstrated above.

It should be noted that there are many possible encodings that arise from the use of an oligomer set; the instant methods focus on the shortest ones. For that purpose, it is necessary to count the number of bits that are needed for a particular encoding. One may assume that an encoding of a sequence consists of units, each of which corresponds either to a letter or to a pointer. Every unit contains a (log 5)-bit field that either indicates a letter or announces a pointer. A unit representing a pointer contains two additional fields having positive integers indicating the position and length of a word, and possibly, in case of the encoding relative to a list of oligomers, a third additional field containing the oligomer index.

If it takes more bits to encode a pointer than to encode the word letter by letter, then it is not worthwhile to use the pointer. Thus, the encoding length of a pointer determines the minimum length of common words that are replaced by pointers in an encoding of minimal length. Note it is not necessary to actually construct encodings—it suffices to estimate the encoding lengths. Thus, one may assume that even more powerful decoding methods would enable smaller pointer sizes. For further details on pointer sizes, see Milosavljevic (1993).

The encodings of minimal length can be computed efficiently by a variation on classical data compression (Storer, 1988). Here, a method for encoding one sequence relative to the other or relative to a list of oligomers is provided. The case when a sequence is self-encoded requires only a slight modification.

The minimal length encoding algorithm takes as an input a target sequence t and the encoding length $p \geq 1$ of a pointer and computes a minimal length encoding of t for a given source s. Since it is only the ratio between the pointer length and the encoding length of a letter that matters, it is assumed without loss of generality that the encoding length of a letter is 1.

Let n be the length of sequence t and let $t_k$ denote the (n−k+1)-letter suffix of t that starts in the $k^{th}$ position. Using a suffix notation, write $t_1$ instead of t. By $I_A(t_k/s)$ is denoted the minimal encoding length of the suffix $t_k$. Finally, let l(i), 1≦i≦n, denote the length of the longest word that starts at the $i^{th}$ position in target t and that can be encoded by a pointer to source s. If the letter at position i does not occur in the source, then l(i)=0. Using this notation, the main recurrence is stated:

$$I_A(t_i/s)=\min(1+I_A(t_{i+1}/s),p+I_A(t_{i+l(i)}/s))$$

Proof of this recurrence can be found in (Storer, 1988).

Based on this recurrence, the minimal encoding length now can be computed in linear time by the following two-step method. In the first step, the values l(i), 1≦i≦n are computed in linear time using a directed acyclic word graph data structure that contains the source s (Blumer et al., 1985). In the case when s is a list of oligomers, the pointer structure of the directed acyclic word graph is exploited to efficiently find continuations. In the second step, the minimal encoding length $I_A(t/s)=I_A(t_1/s)$ is computed in linear time in a right-to left pass using the recurrence given above.

As mentioned above, the encoding length need only be estimated—the recognition method does not require that the exact encoding be computed. For example, the pointer sizes may be chosen so that they provide the optimal recognition in practice, even though they may not suffice for correct decoding. In other words, the scoring function may be a heuristic function that does not correspond to the exact coding length but is justified by good practical recognition performance.

A reverse encoding-length based scoring function also may be used. Instead of calculating the number of bits needed to encode sequence t relative to oligomer list s, one calculates the number of bits need to encode s relative to t. Assuming an encoding method that takes into account both mutual overlaps of words in s and their alignment with t, it may concluded that the sequence t that results in a small relative encoding length I(s/t) exhibits a high degree of similarity with the oligomer list s.

D. Assessing Significance of Matches

A method for assessing significance of matches by applying the minimal length encoding approach described above now is presented. It will be demonstrated that every bit of information revealed by a list of oligomers leads to a two-fold improvement of significance of a match. The following definitions are provided to facilitate this demonstration.

The mutual information scoring function I(s;t) is defined as the difference $I_{A_o}(t)-I_A(t/s)$ or, equivalently, $I_{A_o}(s)-I_A(s/t)$. This definition is motivated by the universal definition (e.g., (Chaitin, 1987; Li and Vitanyi, 1993) of mutual information, which is the difference between the universal encoding length of t, and the universal encoding length of t relative to s. Since encoding schemes for $A_o$ and A are not universal, the scoring function is only an approximation of the universal definition of mutual information; the quality of approximation depends on the choice of schemes A and $A_o$. The approximation can, in this case, be justified by the fact that A and $A_o$ indeed capture the kinds of structure that are expected to occur in the sequences. As demonstrated in the previous section, both $I_{A_o}(S)$ and $I_A(s/t)$ can be computed in linear time, and thus I(s;t) can be computed in linear time as well. This is in sharp contrast with the sequence reconstruction problem, which is NP-hard.

It also should be noted that since I(s;t) is only an approximation of mutual information, it may take negative values. Even though the negative values do not imply significant similarity between t and s, they still have some heuristic value in the sense that they indicate degree of dissimilarity and will be considered in the experimental section.

The significance of similarity depends exponentially on mutual information by the following formula:

$$P_o[I(s;t)\geq d]\leq 2^{-d+O(1)}$$

A derivation of this inequality is known. The method of establishing significance by this formula is referred to as the algorithmic significance method.

Mutual information also provides a way of demonstrating that lists of oligomers can serve better as a query than an optimally reconstructed sequence. It will suffice to show that I(s';t)≦I(s;t), where t is the true sequence, s is the list of oligomers, and s' is a reconstruction based on s. Indeed, this inequality can be proven for the generally defined mutual information up to an additive constant:

$$I(s';t)\leq I(s;t)+o(1)$$

This is an algorithmic version of data processing inequality, analogous to the Shannon-entropy version (e.g., Cover and Thomas, 1991). The proof is based on the fact that s' is a result of processing of s. This inequality should not be surprising because algorithmic processing does not increase information obtained by experiments. Being a result of processing of s, the reconstructed sequence s' cannot contain more information about the underlying sequence. In the following, there is presented an example which indicates that I(s';t) may in practice be considerably less than I(s;t), implying that sequence reconstruction may cause significant loss of information.

Going back to the earlier example, the list of oligomers s, the reconstructed sequence s' and the target sequence t are as follows:

oligomer list s:

| 1  | GAAGTTGC |
| 5  | TTGCGCAT |
| 9  | GTATGCAC |
| 13 | CCACAAGT | reconstruction s': CCA?AAGTTGCG?ATGCAC (SEQ ID NO:2)

true sequence t: GAAGTTGCGCATGCACAAGT (SEQ ID NO:1)

Assuming a pointer size of 10 bits (2 bits for the encoding oligomer plus 3 bits to encode the position within oligomer, plus 5 bits to encode length), an optimal encoding of the true sequence relative to the list of oligomers would be I(t/s')= 10+log 5~12, because, as shown above, a single pointer suffices. On the other hand, assuming the same pointer size of 10 bits (5 bits to encode the beginning plus 5 bits to encode length), an optimal encoding of the target would require approximately I(t;s')=38 bits (~8*log 5+2*10), as illustrated by the following parsing:

parsing of t relative to s': G-AAGTTGCG-C-ATGCAC-A-A-G-T

Assuming that the target t does not contain much regularity, and thus it cannot be encoded in less than I(t)=2*20=40 bits, the following values for mutual information are obtained:

I(s;t)=I(t)−I(t/s)=40−12=28 and

I(s';t)=I(t)−I(t/s')=40−38=2

Note that the mutual information of the true sequence exceeds by 26 bits the mutual information relative to the reconstructed sequence. Thus, the reconstructed sequence gives a much less significant match than the list of oligomers.

It also should be pointed out that conditioning of mutual information provides a means of factoring out the bias that is introduced by choosing an incomplete set of oligomers for hybridization. By w, the total set of oligomers that are examined is denoted and $I(s;t/w)=I_A(t/w)-I_A(t/s,w)$ denotes mutual information that is conditional on the choice of oligomers w. To see how the conditioning factors out bias in the choice of w, consider the case where sequence $t_1$ simply happens to contain many words from w, even though it is not related to s. Then $I(s;t_1/w)=I_A(t_1/W)-I(t_1/s,w) \sim I_A(t_1/w)-I_A(t_1/w) \sim 0$ Now, if $t_2$ is related to s, but contains only a subset of words from w that are also in $t_1$, then $I(s;t_2/w)=I_A(t_2/w)-I(t_2/s,w) \sim I_A(t_2/w)-I_A(t_2/s) > 0$ In contrast, the value of mutual information that is not conditional on w would be the same for both $t_1$ and $t_2$, that is $I_A(t_1/s)=I_A(t_2/s)$ and $t_2$ would not be recognized as the only correct match. Thus, conditioning factors out the bias in the choice of w and enables recognition of truly related sequences.

Finally, it should be noted that in practical applications, when computing $I_A(t/s)$, pointers are not restricted to the source s, but also may point to the left in t, in the same manner as in self-encoding. This leads to a correct estimate of relative information when t contains significant internal repetitive patterns.

EXAMPLES

The method for pairwise comparisons using scoring function $I(s;t/w)=I_A(t/w)-I_A(t/s)$ was implemented in C++ on a Sun Sparcstation under UNIX. This program, called SMPL, is available through ARCH Development Corp., Chicago, Ill., as part of the newest version of the software packages DB_DISCOVERY and PYTHIA. The purpose of the experiments was to examine performance of the recognition method for sequence comparisons. The first experiment uses real data, the second uses simulated data and the third uses both types of data. These experiments are based on a control set of nine sequenced genomic DNA clones of average length 1300 basepairs which cover a 12 kB sequenced portion of the dystrophin gene (Pizzuti et al., 1992), as represented in FIG. 1. The fourth experiment describes large scale cDNA analysis.

A. Real Data

The control set of nine clones was interrogated with 109 (mostly 7-mer) probes, listed in FIG. 2, using the SBH technology (Drmanac et al., 1991) as part of a larger experiment (Crkvenjakov et al., 1993; Milosavljevic and Crkvenjakov, 1993). Ideally, hybridization experiments would have revealed for each probe whether or not the complementary oligomer was present in the cloned sequences. Since the clones were obtained by PCR reactions, the orientation of oligomers could not be resolved. In addition, due to inaccuracy in the experiment, the presence of oligomers could be only determined within a certain degree of error.

For each clone, a source list s consisting of 28 (approx. ¼ of the total) oligomers plus 28 reverse complements, representing a total of 56 oligomers, was compiled based on the highest hybridization scores using a calibration procedure. As an example, the oligomer list s for clone $C_5$ (also denoted by $C'_5$) is given in FIG. 3. The list w consisted of 218 oligomers (109 oligomers from FIG. 2) plus their reverse complements. When computing $I_A(t/s)$, the pointer size was set to 10 bits and, for $I_A(t/w)$, the pointer size was set to 10.3 bits. The pointer sizes were chosen heuristically as giving the best results across a wide range of data, including many cDNA clones.

The oligomer lists were compared against the known DNA sequences of the clones. Table 1 contains the results of comparisons using scoring function $I(s;t/w)$:

TABLE 1

Recognition of known DNA sequences (C) based on oligomer lists (C'). Three largest scores per row are listed; the largest score in each row correctly identifies corresponding clone. Relative score is the difference between the largest and the second largest score in a row.

|     | $C'_1$ | $C'_2$ | $C'_3$ | $C'_4$ | $C'_5$ | $C'_6$ | $C'_7$ | $C'_8$ | $C'_9$ | rel. score |
|-----|-----|-----|-----|-----|-----|-----|-----|-----|-----|------------|
| $C_1$ |     | 6   | 3   |     |     |     |     | 1   |     | 3          |
| $C_2$ |     | 8   |     |     |     | −11 | −11 |     |     | 19         |
| $C_3$ |     |     |     | 34  |     | 16  | 11  |     |     | 18         |
| $C_4$ |     |     | 3   |     | 6   |     | 4   |     |     | 2          |
| $C_5$ |     |     |     |     |     | 25  | 18  |     |     | 7          |
| $C_6$ | 9   |     |     |     | 1   | 3   | 16  |     | 1   | 13         |
| $C_7$ |     |     | 3   |     |     |     |     | 11  | 1   | 8          |
| $C_8$ |     |     | 8   |     |     | 1   |     |     | 13  | 5          |
| $C_9$ |     |     | 9   |     |     | 1   |     |     |     | 11         |
|     | 20  |     |     |     |     |     |     |     |     |            |
|     |     |     |     |     |     |     | average relative score |     |     | 10         |

Rows correspond to known sequences of the clones ($C_1, \ldots, C_9$) while columns correspond to oligomer lists ($C'_1, \ldots, C'_9$). Note that in every row, the highest value occurs in the correct column, indicating that all clones can be correctly recognized using their sequences as queries. The difference between the highest and second-highest score in each row, which referred to as relative score, indicates quality of recognition; the values of relative scores for each row are listed in the rightmost column.

As an example of highly significant correct recognition, the following is the parsing of a segment of clone $C_5$ relative to $C'_5$:

```
TCCTTTAA-A-AAGTGC-T-T-T-A-G-AATTTTC-TTCAATC-A-CTAATAAC-CATGGT-A-A
-G-G-T-AAAGCT-G-A-A-G-AGCAGCT-AAAGGG-A-G-AGCTGAAGAGCAGCTAAA-C-T-T
-GGCTTT-G-A-CATTTTTGTAC-T-C-TTTTTTT-G-CCTTCT-C-T-CAACTCCA-A-AGCAC
CA-G-TGTGCTCT-T
```

AGCTGAAGAGCAGCTAAA is SEQ ID NO:7 and CATTTTTGTAC is SEQ ID NO:8.

A more detailed examination revealed that most, but not all, of the long uninterrupted words in this segment come from repetitions within the clone itself rather than being recognized by overlapping oligomers. As the amount of hybridization data increases, ever longer segments will be recognized by overlapping oligomers, thus improving significance of recognition.

A closer look at how well the experimentally obtained lists of oligomers reflect the true sequence is provided. As an example, first consider the oligomer list $s=C'_5$ for clone $C_5$ in FIG. 3. In order to estimate the sensitivity of hybridization experiments in detecting complementary oligomers, list w must be considered. Out of a total of 16 oligomers from w that contain a 7-mer from $C_5$, a total of 13 also occur in s. Thus, the true positive rate for 7-mers is 13/16=81%. If one considers 6-mers, the situation is much worse. Out of a total of 82 positive oligomers in w, only 33 also occur in s. Thus, the true positive rate for 6-mers is 33/82=40%.

One may view s as being a sublist of w that is enriched for oligomers that share long common subwords with the true sequence: only 16/218=7% oligomers from w contain a 7-mer from $C_5$, while for the corresponding source list s the fraction is 13/56=23%. In the case of 6-mers, the fractions are 82/218=37% and 33/56=59%, respectively. The statistics for clone $C_5$ as well as for other clones are summarized in Table 2:

TABLE 2

Oligomer recognition statistics for the experiment with real data. The first two colunms give counts of oligomers (both in terms of an absolute count and in terms of a percentage of total) in s and w that share a 7-mer with the clone sequence. The third column gives the ratio of oligomers in s and w, i.e., the true-positives ratio. The last three columns contain the same statistics for 6-mers.

|  | common 7-mers | | | common 6-mers | | |
| --- | --- | --- | --- | --- | --- | --- |
|  | s | w | s/w | s | w | s/w |
| $C_1$ | 5 9% | 7 3% | 70% | 19 34% | 62 28% | 53% |
| $C_2$ | 13 23% | 16 7% | 81% | 27 48% | 74 34% | 36% |
| $C_3$ | 19 34% | 24 11% | 79% | 35 53% | 94 43% | 37% |
| $C_4$ | 11 20% | 12 5% | 92% | 22 39% | 60 27% | 37% |
| $C_5$ | 13 23% | 16 7% | 81% | 33 59% | 82 37% | 40% |
| $C_6$ | 16 29% | 21 10% | 76% | 30 54% | 76 35% | 39% |
| $C_7$ | 18 32% | 19 9% | 95% | 28 50% | 77 35% | 36% |
| $C_8$ | 12 21% | 16 7% | 75% | 33 59% | 82 37% | 40% |
| $C_9$ | 12 21% | 13 6% | 92% | 26 46% | 58 26% | 45% |
| average | 15 27% | 17 8% | 83% | 28 55% | 73 37% | 39% |

Experiments also were performed with a scoring function I(s;t) that is not conditional on w. As expected, most clones show the highest score with the DNA sequences that happen to have a high content of oligomers from w.

B. Simulated Data

In the previous experiment, the fraction of oligomers from w that contain a 7-mer from the clone was on average 8%, and the fraction for 6-mers was 37% (last row of Table 2). In order to test if similar recognition would be achieved with a set of oligomers that are less representative of the sequence, an independent set of 109 oligomers, plus their reverse complements, with respective fractions of 4% and 28% was used as dictionary w. Signatures s for each clone were then simulated so that the fraction of true positives for both 6-mers and 7-mers was approximately the same as in the experiment with real data. The detailed statistics are in Table 3:

TABLE 3

Oligomer recognition statistics for the experiment with simulated data. The first two columns give countrs of oligomers (both in terms of an absolute count and in terms of a percentage of total) in s and w that share a 7-mer with the clone sequence. The third column gives the ratio of oligomers in s and w, i.e., the true-positive ratio. The last three columns contain the same statistics for 6-mers.

|  | common 7-mers | | | common 6-mers | | |
| --- | --- | --- | --- | --- | --- | --- |
|  | s | w | s/w | s | w | s/w |
| $C_1$ | 7 13% | 8 4% | 88% | 22 39% | 57 26% | 39% |
| $C_2$ | 8 14% | 10 5% | 80% | 28 50% | 69 32% | 41% |
| $C_3$ | 4 7% | 4 2% | 100% | 20 36% | 52 23% | 38% |
| $C_4$ | 6 11% | 7 3% | 86% | 20 36% | 53 24% | 38% |
| $C_5$ | 18 32% | 22 10% | 82% | 33 59% | 86 39% | 38% |
| $C_6$ | 6 11% | 7 3% | 86% | 28 50% | 69 32% | 41% |
| $C_7$ | 4 7% | 4 2% | 100% | 17 30% | 44 20% | 39% |
| $C_8$ | 11 20% | 13 6% | 85% | 28 50% | 67 30% | 42% |
| $C_9$ | 5 9% | 6 3% | 83% | 24 43% | 64 29% | 37% |
| average | 8 14% | 9 4% | 85% | 24 44% | 62 28% | 39% |

The scores with the simulated signatures are given in Table 4:

TABLE 4

Recognition based on combined oligomer lists C'. The largest score in each row correctly identifies the corresponding clone. Relative score is the difference between the largest and the second largest score in a row.

|  | $C'_1$ | $C'_2$ | $C'_3$ | $C'_4$ | $C'_5$ | $C'_6$ | $C'_7$ | $C'_8$ | $C'_9$ | rel. score |
| --- | --- | --- | --- | --- | --- | --- | --- | --- | --- | --- |
| $C_1$ | 2 | −4 |  |  |  | 0 |  |  |  | 2 |
| $C_2$ |  | 20 |  | −4 |  |  |  | 6 |  | 14 |
| $C_3$ |  |  | 25 |  | 13 |  |  |  | 14 | 11 |
| $C_4$ |  | 0 |  | 18 | 3 |  |  |  |  | 15 |
| $C_5$ | −7 |  |  |  | 27 |  | −10 |  |  | 34 |
| $C_6$ |  |  |  |  | 12 | 34 |  | 10 |  | 22 |
| $C_7$ |  | 4 |  |  | 2 |  | 9 |  |  | 5 |
| $C_8$ | 5 |  |  |  |  |  | 12 | 35 |  | 23 |
| $C_9$ |  |  |  |  | 0 | 0 |  |  | 11 | 11 |
|  |  |  |  |  |  |  | average relative score |  |  | 15 |

In order to compare the experiments with real and simulated data, criteria for quality of recognition in a particular experiment must be defined. Good sequence recognition may be characterized by a large difference between the highest and the second-highest score in a particular row; this is referred to as a relative score. The average relative score for all rows in a table reflects the overall quality of recognition. For the real data, the average relative score is 10, while for the simulated data the score is 15.

It was somewhat surprising to obtain better recognition with probes that are less representative of the sequence. One possible explanation is that, in the simulated experiment, all the relevant statistics and dependencies of the real experiment were not considered. The simulated experiment still provides a clear indication that sequence recognition may not critically depend on the choice of probes.

C. Real and Simulated Data

The goal of this last experiment was to determine how rapidly recognition improves as new hybridizations are performed. For this purpose, the data from the real and the simulated experiment were merged together to create a single experiment: a new dictionary w (consisting of 218 probes and their reverse complements) was formed by concatenating dictionaries from the two previous experiments. Source oligomer lists for each clone also were obtained by simple merging.

The scores are given in Table 5:

TABLE 5

Recognition based on combined oligomer lists C'. The largest score in each row correctly identifies the corresponding clone. Relative score is the difference between the largest and the second largest score in a row.

| | $C'_1$ | $C'_2$ | $C'_3$ | $C'_4$ | $C'_5$ | $C'_6$ | $C'_7$ | $C'_8$ | $C'_9$ | rel. score |
|---|---|---|---|---|---|---|---|---|---|---|
| $C_1$ | 5 | -9 | | | | | | | -9 | 14 |
| $C_2$ | | 14 | | | -23 | -24 | | | | 37 |
| $C_3$ | | | 33 | -1 | 6 | | | | | 27 |
| $C_4$ | | | | 16 | -12 | -15 | | | | 28 |
| $C_5$ | | | | -16 | 13 | -13 | | | | 26 |
| $C_6$ | | | | -5 | -2 | 15 | | | | 20 |
| $C_7$ | | -4 | | | | | 15 | 1 | | 14 |
| $C_8$ | -12 | -11 | | | | | | 21 | | 32 |
| $C_9$ | | -19 | | | -21 | | | | 7 | 26 |
| | | | | | | | | average relative score | | 25 |

The average relative score is 25, which equals the sum of the relative scores in the previous two experiments (10+15). In retrospect, this result may have been expected because the dictionaries from the two previous experiments contain non-overlapping sets of probes, each providing independent evidence for the identity of clones. In any case, this experiment indicates that, on average, around 1 bit of recognition specificity (which corresponds to a twofold improvement in significance level) is gained per 10 probes.

D. Discovery of Genes from an Infant Brain cDNA Library

One of the goals of the Human Genome Project is the sequencing of all human genes. An intermediate and currently feasible step toward this goal is the sequencing of cDNA fragments, referred to as expressed sequence tags (EST-s) (Adams et al., 1991). EST strategy relies on a "one at a time" random sampling of cDNA libraries, with the result that every second or third sequence is needlessly resequenced, depending on the library used. Over 40,000 distinct ESTs have been compiled so far by this method (Khan et al., 1992; Matsubara & Okubo, 1993; Adams et al., 1993). As the number of sequenced cDNAs grows, the resequencing problem inevitably will worsen. In order to reduce resequencing, the libraries are typically normalized by biochemical procedures (Soares et al., 1994). In the normalized libraries, relative abundancies of the most frequent and rarest cDNAs are equalized to a large degree, but the chance of finding a new gene is not expected to more than double (Drmanac et al., 1994b). The EST resequencing problem is exacerbated by the fact that many genes are expressed in multiple libraries. Two cDNA clones may not even be recognized as identical by the EST strategy because the sequenced fragments may not overlap.

While beneficial for discovering new genes, normalized libraries do not permit accurate quantification of the abundancy of individual RNAs, which is a necessary step in understanding of mammalian gene expression. In order to quantitatively study expression of genes across different cell types, developmental stages, and physiological conditions, hundreds of thousands, and perhaps millions of clones from a number of potentially highly redundant non-normalized cDNA libraries must be comparatively studied. Redundancy also may be profitably employed for complete cDNA sequencing. For example, an average 3–6 kB mRNA can be efficiently sequenced by current methods based on up to 10 overlapping cDNAs from various libraries. All of the foregoing puts a premium on a method that enables rapid and economical mutual clone comparisons and comparisons of clones against previously sequenced DNA.

It has been estimated that oligomer sequence signatures (OSS-s) consisting of 100–1000 probes would enable precise mutual comparisons of clones as well as comparisons of clones against DNA sequence databases (Drmanac et al., 1991; Lennon and Lehrach, 1991). The data production lines that are being developed for the purpose of sequencing by hybridization (SBH) can in fact be easily employed for rapid generation of OSS-s (Drmanac and Drmanac, 1994; Drmanac et al., 1992a; 1992b; Grujic et al., 1994; Meier-Ewert et al., 1993). Densely arrayed clones can be examined at a 10- to 100-fold higher rate, and much more economically, than by standard sequencing. Thus, data throughputs required for exhaustive gene discovery and for detailed studies of expression patterns can be achieved.

A pilot study is presented here using methods for mutual clone comparison and for comparison of clones against known DNA sequences. This analysis involves 29,570 cDNA molecules from the recently developed human infant brain cDNA libraries (Soares et al., 1994). For the purpose of this study, more than ten million individual clone/probe hybridization experiments were performed. A complementary study utilized the same data production line, but is based on an independent collection of hybridization data that were analyzed using an independent set of data analysis methods. These two studies demonstrate unique opportunities in genome-scale cDNA analysis that are made possible by large-scale hybridization experiments.

Clones from the original and normalized versions of the human infant brain cDNA libraries (Soares et al., 1994) were arrayed and immobilized on nylon filters as PCR products by applying previously described techniques (Drmanac and Drmanac, 1994; Drmanac et al., 1992a; 1992b; Grujic et al., 1994;). In the following discussion, two physical filters are of the same type if they contain the same cDNAs that are spotted using the same pattern; i.e., two replicas of filters belong to the same filter type. Each type of filter contained a set of clones spotted in duplicate.

A total of 11 filter types were created (see Table 6): 8 small filter types contained 3,456 dots each, arrayed on a 8×12 cm surface; 2 medium filter types contained 7,776 dots each, arrayed on a 8×12 cm surface; 1 large filter type contained 31,104 dots arrayed on a 16×24 cm surface. A common set of 107 heptamers was hybridized with each of the 11 distinct filter types (for an example of a hybridization experiment, see FIG. 4). Several physical copies of each type of filter were prepared in order to parallelize hybridization experiments. Each physical copy of a particular type of filter was hybridized with a different subset of heptamer probes (probe list available on request). The results obtained with all filter replicas were pooled together to give OSS-s consisting of hybridization intensities for the entire probe set.

TABLE 6

Summary of filter types used in hybridization experiments. A fraction of dots spotted on each type of filter contained control clones: 11.1% on small filters, 3.7% on medium filters, and 1.25% on large filters.

| filter format | total filter types | dots per filter | dots scored | cDNAs scored | false separation of repeated dots (%) |
|---|---|---|---|---|---|
| small | 8 | 3,456 | 24,353 | 11,078 | 1 |
| medium | 2 | 7,776 | 13,461 | 6,810 | 5.5 |
| large | 1 | 31,104 | 23,448 | 11,682 | 4.5 |

In order to achieve reproducibility of individual clone/probe hybridization intensities across different filters despite variations in experimental conditions, two scaling steps were performed. To estimate relative molarity in individual dots, each physical copy of a filter was hybridized with a mass probe which consisted of an oligomer that was complementary to the primer region of cDNA PCR products.

In the first scaling step, in order to factor out differences in molarity of cDNA in individual dots, the hybridization intensities of each probe were divided by the hybridization intensities of the mass probe. The dots that did not give hybridization intensities with the mass probe above a pre-specified threshold were considered empty and all hybridizations with them were discarded from further analysis.

In the second scaling step, the mass-scaled intensities of each dot were replaced by their rank value among all others on the same filter. While the first (mass-scaling) step achieves reproducibility across different dots on the same filter, the second (rank-scaling) step achieves reproducibility across different filters, regardless of their size, due to the fact that they all contain large numbers of clones from the same library.

Sequence signatures for particular clones were compiled by pooling rank-scaled hybridization intensities across different physical copies of a particular filter type. Signatures that were missing more than 25% hybridization values (due to empty dots) were discarded from further analysis. A clustering analysis was then applied to group the signatures into disjoint clusters according to their mutual similarities.

Two independent approaches were applied in order to estimate clustering error: (i) individual cDNAs are spotted in duplicate and (ii) groups of highly overlapping control clones of known sequence were spotted along with the cDNAs. The degree of false separation into disjoint clusters of signatures that come from identical or highly overlapping clones, as well as the degree of false joining of non-overlapping control clones into identical clusters, was used as an estimate of clustering error.

Each of the 8 small filters contained a set of 1,728 cDNAs from the original human infant brain library (Soares et al., 1994), spotted in duplicate. The two medium filters contained 3840 and the large filter contained 15,867 duplicates from the normalized version (Soares et al., 1994) of the same library. The clustering error, estimated as the percentage of dots that do not occur together with their duplicate in the same cluster, ranged from 1% on the small filters to 5.5% on medium filters, as indicated in Table 6.

These results indicate a high reproducibility for hybridization experiments and low clustering error rate for all filter formats and array densities. The actual failure rate of clustering is even smaller because the signatures whose duplicates were eliminated due to missing values also were counted as clustering failures. The slight loss of accuracy on medium and large filters may be justified by an almost 10-fold increase in hybridization throughput per filter.

Figure 4:
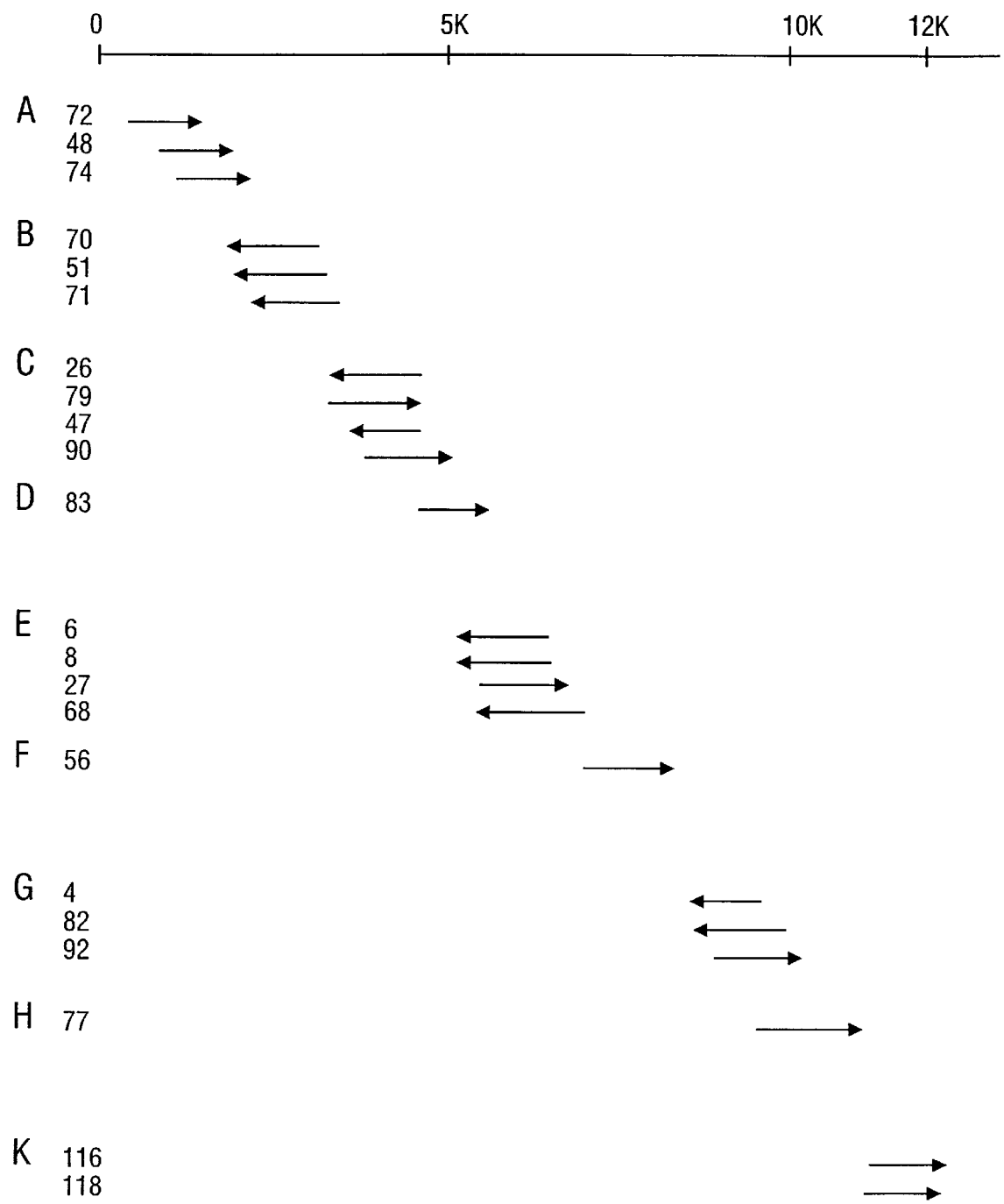
FIG. 4: The set of control clones from the Dystrophin gene intron that are used as benchmark for clustering. The clones are selected so that there are 9 groups of clones (denoted by letters A through K) with a 50% overlap within groups and less than 50% overlap across groups.

In addition to the cDNAs, each of the filters contained several independent amplifications of a set of 46 clones of known sequence as controls (Pizzuti et al., 1992). The control clones were 1 to 2 kB in length and they cover a 12 kB sequenced portion of the human dystrophin gene intron segment. Each control clone was multiply spotted on each of the filters (Table 6). A subset of the clones that are actually used as a benchmark are depicted in FIG. 4. This set of clones was chosen so that there are nine distinct groups where clones within a group overlap by at least 50%, and clones across different groups overlap by less than 50%. (Theoretical analysis indicates that an overlap of 50% is equivalent to a homology of 80% in terms of OSS similarity.) The presence of identical and highly overlapping control clones across different filters enabled the testing whether identical or highly similar clones are grouped together by the clustering algorithm despite the fact that they are spotted on different filters and separately hybridized. The clustering of control clones spotted on all eight small filter types is summarized Table 7.

TABLE 7

Clustering of control clones depicted in FIG. 4. Columns correspond to groups of overlapping clones. Rows correspond to clusters obtained by the algorithm based on signatures obtained from all eight small filters. The error of false separatino, estimated by dividing the number of clones i nsplinter clusters by the total number of clones outside "garbage" clusters is 45%. Theoretical analyses show that the probability of false joining of two signatures is at most $10^{-5}$, which is consistent with the experimental results: 1 false joining (0.13%) in cluster 12 resulted from more than 100,000 pairwise comparisons. However, even that single false joining may be a result of sample contamination rather than clustering error.

|    | A   | B   | C   | D  | E   | F  | G   | H | K | total |
|----|-----|-----|-----|----|-----|----|-----|---|---|-------|
| 1  | 131 |     |     |    |     |    |     |   |   | 131   |
| 2  | 2   |     |     |    |     |    |     |   |   | 2     |
| 3  |     | 126 |     |    |     |    |     |   |   | 126   |
| 4  |     | 7   |     |    |     |    |     |   |   | 7     |
| 5  |     | 2   |     |    |     |    |     |   |   | 2     |
| 6  |     |     | 150 |    |     |    |     |   |   | 150   |
| 7  |     |     | 2   |    |     |    |     |   |   | 2     |
| 8  |     |     | 2   |    |     |    |     |   |   | 2     |
| 9  |     |     | 2   |    |     |    |     |   |   | 2     |
| 10 |     |     | 5   |    |     |    |     |   |   | 5     |
| 11 |     |     | 2   |    |     |    |     |   |   | 2     |
| 12 |     |     | 2   |    |     |    |     | 1 |   | 3     |
| 13 |     |     |     | 52 |     |    |     |   |   | 52    |
| 14 |     |     |     |    | 164 |    |     |   |   | 164   |
| 15 |     |     |     |    | 1   |    |     |   |   | 1     |
| 16 |     |     |     |    | 7   |    |     |   |   | 7     |
| 17 |     |     |     |    |     | 44 |     |   |   | 44    |
| 18 |     |     |     |    |     |    | 148 |   |   | 148   |
| 19 |     |     |     |    |     |    | 5   |   |   | 5     |

TABLE 7-continued

Clustering of control clones depicted in FIG. 4. Columns correspond to groups of overlapping clones. Rows correspond to clusters obtained by the algorithm based on signatures obtained from all eight small filters. The error of false separatino, estimated by dividing the number of clones i nsplinter clusters by the total number of clones outside "garbage" clusters is 45%. Theoretical analyses show that the probability of false joining of two signatures is at most $10^{-5}$, which is consistent with the experimental results: 1 false joining (0.13%) in cluster 12 resulted from more than 100,000 pairwise comparisons. However, even that single false joining may be a result of sample contamination rather than clustering error.

|           | A   | B   | C   | D  | E   | F  | G   | H  | K   | total |
|-----------|-----|-----|-----|----|-----|----|-----|----|-----|-------|
| 20        |     |     |     |    |     |    |     | 40 |     | 40    |
| 21        |     |     |     |    |     |    |     |    | 89  | 89    |
| 22        |     |     |     |    |     |    |     |    | 4   | 4     |
| discarded | 23  | 20  | 28  | 4  | 37  | 10 | 9   | 7  | 15  | 153   |
| total     | 156 | 155 | 193 | 56 | 209 | 54 | 162 | 48 | 108 | 1141  |

An additional feature of the clustering analysis, compared to the one described, was that there was a "garbage" cluster (bottom row in Table 7). All the clusters that contained signatures whose average mutual similarity was larger than a prespecified threshold were assigned to it. Only 0.13% of non-overlapping clones were falsely joined together into the same cluster, and only 4.5% of overlapping clones were falsely split across different clusters. The low error rate indicates the ability of the clustering analysis to recognize significantly overlapping or homologous clones even if they are spotted on different filters. Indeed, the single case of false joining was most likely due to contamination of samples.

The observed grouping of overlapped control clones demonstrates that existing contigs for complete sequencing of long cDNAs have been assembled to the extent allowed by the directional nature of the library. The low rate of false joining is further supported by the fact that none of the clusters in the final clustering of all the signatures contained both a cDNA clone and a control clone. This was indeed expected because the control clones come from an intronic region. Since tens of thousands of cDNA clones were clustered together with one thousand control clones, this indicates that the probability of false joining is less than one in ten million pairwise comparisons.

The pattern of false splitting (Table 7) indicates that, for most large clusters, there are a few "satellite" clusters containing apparently dissimilar signatures. The rate of 4.5% indicates that the number of distinct cDNA clones in the final clustering experiment may be slightly overestimated. A number of small "satellite" cDNA clusters may contain clones that are highly similar to clones from a larger cluster, but are not detected as such.

The goal of a first cDNA clustering experiment was to compare clone abundancies in original and normalized human infant brain libraries. Clone abundancies in the normalized library were shown to exhibit less variation than the abundancies in the original library, thus facilitating more efficient gene discovery. The measured abundancy structures of 11,078 independent clones from the original library and 10,340 from the normalized library are shown in Table 8.

TABLE 8 cDNA abundancies in original and normalized infant brain libraries, as compared with calculated abundancies for rat brain. The abundancies are estimated within a factor of two; for example, some of the 84 cDNAs species assigned to the abundancy class 0.2 may in fact belong to the abundancy classes 0.1 or 0.5. In light of this degree of precision, the disagreement between the rat and original human libraries at the abundance level 0.2 may not be significant.

|                | Number of cDNA species | | |
|----------------|---|---|---|
| Abundance      | calculated for rat brain library ((Milner & | human infant brain library | |
| class (%)      | Sutcliffe 1983), Table 7) | original (11,078 clones) | normalized (10,340 clones) |
| ≧1             | 13   | 8    | —    |
| 0.5            | 11   | 13   | 4    |
| 0.2            | 23   | 84   | 21   |
| 0.1            | 146  | 150  | 51   |
| 0.05           | 456  | 443  | 429  |
| 0.02           | 290  | 668  | 1032 |
| ≦0.01          | 1520 | 3529 | 6703 |
| total species: | 2459 | 4895 | 8246 |
| average abundance: | 0.04 | 0.02 | 0.01 |

The average abundance of individual cDNA was 0.02% for the original library and 0.01% for the normalized; the original library contained 3-fold more clusters that achieve abundancy of 0.1% or more. Apparently, normalization did not affect the total number of moderate and low abundancy clusters, while at the same time it significantly reduced the number of high abundancy clusters. Clone identification (described below) allowed a demonstration that the normalization was extremely successful for the most frequent RNAs: the abundancies for tubulin alpha, elongation factor alpha 1, and cytoskeletal gamma actin RNAs fell 35-, 32- and 10-fold respectively (Table 10).

The results indicate the biochemical normalization did not increase the number of distinct cDNAs in a randomly drawn sample of about 10,000 clones by more than 90%. An approximately two-fold increase also is expected on statistical grounds (Drmanac et al., 1994b).

The most abundant cDNAs in brain account for a lesser fraction of total RNA than in other differentiated tissues like muscle or liver (chikaraishi, 1979; Milner and Sutcliffe, 1983). The results confirm this: depending on the sample size (the maximal sample consisting of 11,078 clones represented in Table 8), on average, one out of every 1.5–2.3 clones from the original brain library contained a distinct sequence.

The goal of the final cDNA clustering experiment was to count the total number of distinct genes represented in the sample by clustering together signatures of all 29,570 clones from both original and normalized libraries. The clustering analysis produced 16,741 clusters, each corresponding to a distinct cDNA. A total of 12,363, or 74%, of all clusters contained single clones. Some of these single clones might represent subfunctional RNAs, nuclear leakage, or a subfunctional readthrough from nonbrain genes.

Figure 5:
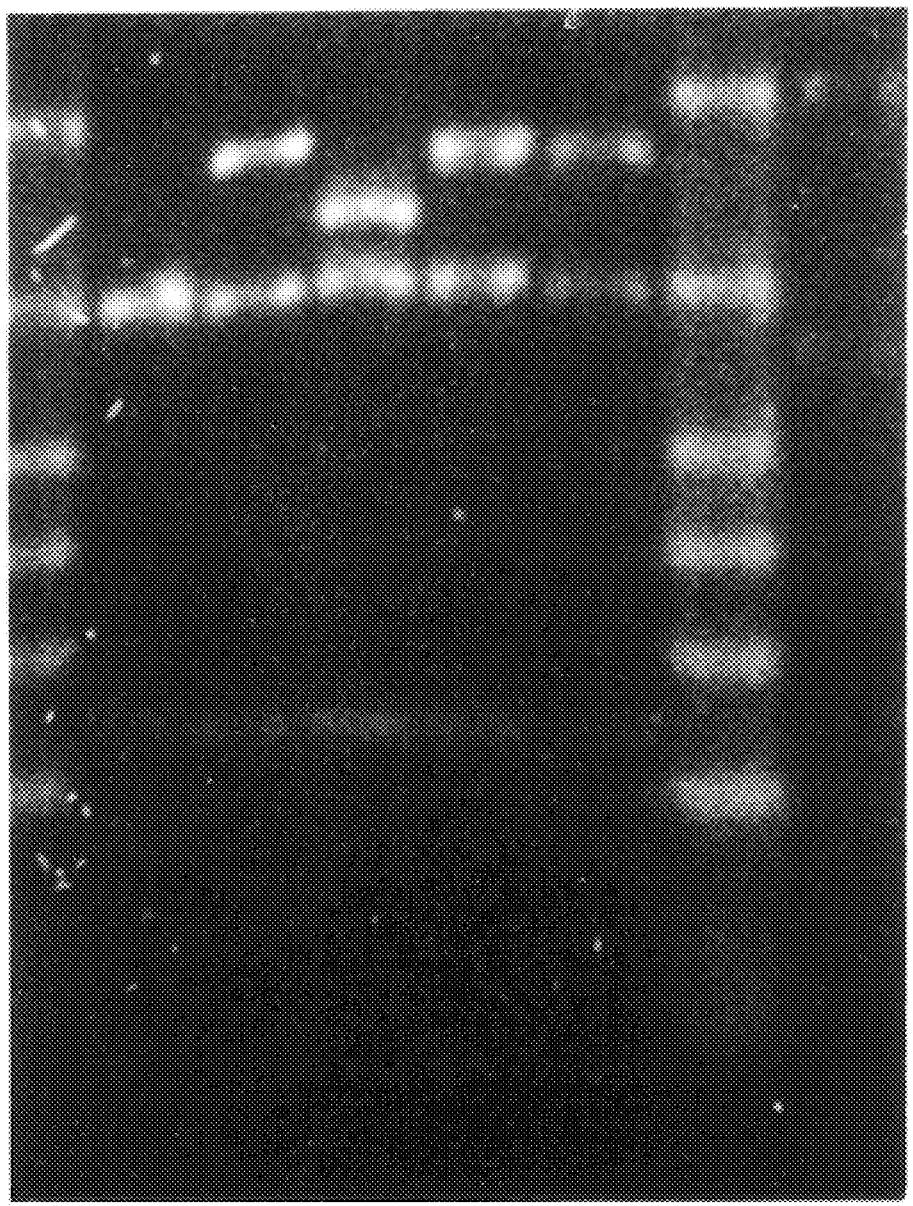
FIG. 5: The restriction enzyme analysis of five cDNAs from the largest cluster (hypothesized and confirmed as elongation factor 1 a cDNA; see Section D of the Detailed Examples herein. The first cDNA provided seed signature for clustering and searches, the remainder was randomly drawn from individual subclusters obtained by clustering at higher stringency than used for the original clustering (the higher stringency of clustering enables detection of finer differences between the clones from the same cluster). Lanes 1 and 7 contain marker hin F pBR322; lanes 2–6 contain the 5 clones. The pattern is consistent with identity in regions of overlap.

To further demonstrate that the cDNA clustering procedure is reliable, the individual cDNAs from some clusters were mapped by restriction enzymes. A typical result from such an experiment is shown in FIG. 5, where five clones picked randomly out from 525 clones from the most abundant cluster, representing elongation factor alpha 1 cDNA (identified as described bellow), share at least two fragments totaling 1000 bp, presumably from the common 3'-end. This confirms the expected homogeneity of clones within the cluster.

In addition to the restriction analyses, cDNAs from a few of the clusters also were sequenced from both ends. The sequencing confirmed homogeneity within clusters. For example, end-sequencing of 4 clones from a gamma actin cluster and 5 clones from elongation factor alpha 1 cluster (examined by restriction analysis in FIG. 5) revealed that the clones from the same cluster share essentially the same sequence, except that 5' ends of individual clones started at variable positions within the gene as much as 200 bp apart.

A further step in the characterization of cDNAs was a systematic recognition of the genes that give rise to the identified clusters. The lists of oligomers that were putatively identified to occur in particular clones were compared against known DNA sequences in order to identify genes that have already been sequenced. In the following, there is presented a brief outline of the recognition experiment.

For each hybridization signature consisting of 107 hybridization intensities, a list consisting of the 28 oligomer probes (roughly one quarter) that exhibit the highest intensities was compiled. The list of 28 oligomers was augmented by the additional 28 reverse complementary oligomers due to the fact that both strands of PCR products were hybridized and the orientation of oligomers could not be resolved. Since the number of oligomers used was small, in order to correctly recognize similarities it was necessary to somewhat restrict the searches. For that purpose, only the 100 most frequent (as determined by cluster size) cDNAs from the original (non-normalized) infant brain library were compared with sequences of 195 genes expected to be highly to moderately expressed in the brain. In order to identify the most frequent cDNAs, the clones from the original library were clustered at high stringency (to maximize homogeneity of clones within clusters) and a single representative from 100 largest clusters was selected. The corresponding 100 oligomer lists were used as a database for searches using known DNA sequences as queries. A total of 195 searches involving gene sequences of average length 2.5 kB were performed against the database consisting of the 100 oligomer lists.

Significance of similarity between a sequence and a list was determined by the analytical significance method: for each sequence and a candidate oligomer list, it was estimated how many bits of information about the sequence are revealed by the list; every bit of information implies a two-fold improvement in significance value of the particular match. Two parameters were considered for each query sequence—the top score with a particular oligomer list and the difference between the top score and the second highest score, termed absolute and relative scores, respectively. A list of all the sequences that resulted in a relative score of 10 bits or more were further considered. Some inconsistencies (different sequences matching the same clone) were resolved by selecting the one with the highest absolute score. This resulted in a set of 21 matches. It was hypothesized that these matches are due either to sequence identity or to high sequence similarity.

In order to test the putative identifications, the 5'-ends of 18 clones (average length 300 bp) were obtained by single-pass sequencing on an ABI sequencer. The three remaining clones (out of a total of 21) could not be sequenced due to technical problems. The sequences were then used in a BLAST search against GenBank. The sequenced fragments, BLAST matches and the hypothesized sequences were then pairwise aligned. The results of the analysis of alignments are summarized in Table 9.

TABLE 9

Recognition of sequence identities and similarities by comparison of 100 oligomer lists against 195 GenBank entries. Out of 18 putative recognitions, 6 identities and 5 significant similarities were confirmed by single pass gel sequencing and subsequent BLAST search of GenBank. An identity was considered confirmed if it occurred as the top-scoring entry of a BLAST search. The numbers of mutations indicated in the bottom table include single-pass sequenceing errors.

| Exact identifications | |
| --- | --- |
| hyposthesized based on hybridization to short oligomers | top GenBank score in a BLAST search using a 5' single-pass sequence as a query |
| 1. elongation factor alpha 1 | elongation factor alpha 1 |
| 2. macmarcks mRNA | macmarcks mRNA |
| 3. calmodulin | calmodulin |
| 4. hexokinase | hexokinase 1 |
| 5. thyrdoid hormone receptor alpha | thyroid hormone receptor alpha |
| 6. ADP-ribosylation factor alpha | ADP-ribosylation factor alpha |

TABLE 9-continued

Recognition of sequence identities and similarities by comparison of 100 oligomer lists against 195 GenBank entries. Out of 18 putative recognitions, 6 identities and 5 significant similarities were confirmed by single pass gel sequencing and subsequent BLAST search of GenBank. An identity was considered confirmed if it occurred as the top-scoring entry of a BLAST search. The numbers of mutations indicated in the bottom table include single-pass sequenceing errors.

Significant similarities

| hyposthesized based on hybridization to short oligomers | top GenBank score in a BLAST search using 5' single-pass sequence as a query | hypothesized/GenBank alignment | | | |
|---|---|---|---|---|---|
| | | length | indels | point-mutations | transition |
| 1. elongation factor gamma 1 | pancreatic tumor-related protein | 58 | 1 | 17 | 4 |
| 2. glial fibr-acid | rat dynein-associated protein | 172 | 8 | 56 | 22 |
| 3. adaptin b | HDL-binding protein | 54 | 0 | 23 | 10 |
| 4. 80K-H protein | anonymous EST | 56 | 2 | 17 | 10 |
| 5. cAMP-d kinase Ia | initiation factor 4Ia | 51 | 1 | 14 | 6 |

TABLE 10

Abundancies of identified clones in original and normalized cDNA libraries, as determined by OSS clustering and gel-based sequencing. The starred entries denote abundancies estimated based on clustering of OSS-s in the complementary study. The missing values could not be reliably estimated due to missing data, uncertain correspondencies and other problems.

Abundancies of identified clones

| clone | original library | | normalized library | original/normalized |
|---|---|---|---|---|
| | oss | gel | oss | abundance ratio |
| tubulin alpha | 2.58/1.7* | 2.69 | 0.74/0.82* | 34.87 |
| elongation factor alpha 1 | 2.83/2.53* | 3.06 | 0.88/0.33* | 32.16 |
| cytoskeletal gamma actin | .47/24* | .43 | .022* | 10.1* |
| cytochrome b1+ | .044* | | .072* | .61* |
| voltage dependent channel | .018/.022* | | .066* | .33* |
| olfactomedin | .045 | | .299* | .15* |
| mitochondrial genome 1700–2100 | .722/.48* | | .249/.299* | 2.89/1.6* |
| 90 kD heat shock | .180 | .18 | .027 | 6.66 |
| ubiquitin | .144 | .06 | .022 | 6.54 |
| thyroid hormone receptor | .144 | .12 | .011 | 13.09 |
| G(s) alpha | .135 | .06 | .016 | 8.44 |
| G(s) alpha | .135 | | | |
| alpha collagen-like | .117 | | | |
| ADP-ribosylation factor | .091 | .12 | .011 | 8.27 |
| calmodulin | .091 | .43 | .038 | 2.39 |
| hexokinase 1 | .081 | .06 | .005 | 16.2 |
| macmarcks mRNA | .072 | | | |
| elongation factor 1 gamma | .261 | .24 | | |
| enonymous | .081 | | .011 | 7.36 |
| mitochondrial genome 2660–3100 | .099 | | | |

In 11 (out of a total of 18) cases, the BLAST search confirmed the putative identification. The first 6 items represent 6 confirmed identities followed by 5 confirmed similarities. The remaining 7 identifications were not confirmed by BLAST searches. In most of the 7 unconfirmed cases, the sequences that were identified by BLAST were not present in the selected set of 195 genes. In 4 of the 7 cases, due to the absence of identical sequences in the selected set, the sequences that exhibit significant similarity to the identical sequences turned up as best matches instead. There was only one case where a sequence returned by BLAST search was also present in the selected set but was not recognized.

In addition to the GenBank search, the gel-sequenced fragments also were used as queries in a search of dbEST. All of the searches identified either highly similar or identical sequences, indirectly confirming that frequently expressed genes were chosen for the comparisons.

As a preliminary test of the possibility of cross-correlation of OSS data across different laboratories, the hybridization experiments reported in the complementary study were coordinated with the experiments so that a portion of clones from the other study were hybridized with the same set of 107 probes. A total of about 22,000 signatures from the two laboratories were clustered together using the described method. A significant degree of cross-correlation was confirmed by correct grouping of control clones of known sequence from the two data sets. Correspondence between a number of clusters obtained in the two studies could be established and the abundancy information could be integrated, as shown in Table 10. A number of clusters from individual laboratories were identified by gel-sequencing of individual members and by subsequent database searches. By cross-correlating the data across different laboratories, a number of clusters could be identified without sequencing.

Moreover, the published abundance information that is obtained through EST gel sequencing of the same library could be compared against abundancies obtained by the clustering experiments. The results (shown in Table 10) indicate an excellent agreement of EST gel sequencing and the results on the abundances of elongation factor alpha, tubulin alpha and gamma actin cDNAs, the first two being the most prevalent species in the library. The seven-fold smaller sample size in the gel-based study does not allow a comparison of abundances of remaining cDNAs. The extent of agreement of abundancies obtained from the independent hybridization experiments of the two laboratories demonstrates the possibility of cross-correlation of independently obtained OSS-s.

The gel-based EST sequencing and analysis (Adams et al., 1991; Khan et al., 1992; Matsubara and Okubo, 1993; Adams et al., 1993) has already demonstrated that commercial cDNA libraries, while adequate for screening with specific probes, are not very useful for systematic gene discovery and for gene expression studies. The high fraction of contaminating mitochondrial and ribosomal sequences and various cloning and amplification biases make for an unacceptably high sampling redundancy. Also, it is important to use cDNA libraries which do not exhibit any cloning bias, which may distort the true gene expression pattern. Several EST studies (Khan et al., 1992; Matsubara and Okubo, 1993; Adams et al., 1993) have found that the libraries used in the study are superior to other examined libraries in all important respects.

To check for a possible cloning bias using cDNA, abundance measurements were compared with the earlier estimates for rat brain obtained on RNA directly (Milner and Sutcliffe, 1983). Table 8 summarizes the results of the comparison. Assuming similar abundancy structure in the rat and the original human libraries, the agreement between the abundancies for highly and moderately frequent cDNAs indicates that the original library does not exhibit any major cloning bias. One should note that the abundancies for rat brain are not directly measured, but are calculated by extrapolating from experiments involving fewer than 200 distinct cDNAs. Due to the small size of the sample, the large number of distinct but infrequent cDNAs that are detected by SBH methodology could not be detected in that study. Assuming that the infrequent cDNAs detected in humans also are present in rat, it may be concluded that extrapolation from small samples is not an adequate substitute for large-scale cDNA studies.

REFERENCES

The following references, to the extent that they provide exemplary procedural or other details supplementary to those set forth herein, are specifically incorporated herein by reference:

Adams et al., *Science*, 252:1651–1656, 1991.
Adams et al., *Nature Genetics*, 4:373–380, 1993.
Bell et al., *Text Compression*, Prentice Hall, 1990.
Blaisdell, "A measure of the similarity of sets of sequences not requiring sequence alignment," *Proceedings of the National Academy of Sciences U.S.A.*, 83:5155–5159, 1986.
Blumer et al., "The smallest automation recognizing the subwords of a text," *Theoretical Computer Science*, 40:31–55, 1985.
Chaitin, *Algorithmic Information Theory*, Cambridge University Press, 1987.
Chikaraishi, *Biochemistry*, 18:3249–3256, 1979.
Cover and Thomas, *Elements of Information Theory*, Wiley, 1991.
Crkvenjakov et al., "Analysis of 15,000 human brain cDNA clones for new expressed genes and remapping of previously sequenced human cosmid DNA. In *Genome Sequencing and Analysis Conference V*, 1993.
Drmanac, "Abstract Book for Genome Mapping and Sequencing'" arranged by Richard Myers, David Porteous and Robert Waterstone, *Cold Spring Harbor Laboratories*, p.60, 1994.
Drmanac et al., R., Drmanac, S., Jarvis, J., and Labat, I., "Sequencing by hybridization," In J. Venter, editor, *Automated DNA Sequencing and Analysis Techniques*, pages 29–36, Harcourt Brace Jovanovich, New York, 1994a.
Drmanac et al., "DNA Sequencing determination by hybridization: A strategy for efficient large-scale sequencing," *Science*, 260:1649–1652, 1993.
Drmanac et al., "Partial sequencing by hybridization: Concept and applications in genome analysis. In *The First International Conference on Electrophoresis, Supercomputer and the Human Genome*," pages 60–74, World Scientific, Singapore, 1991.
Drmanac and Crkvenjakov, "Method of sequencing of genomes by hybridization of oligonucleotide probes," U.S. Pat. No. 5,202,231, 1993.
Drmanac and Drmanac, *BioTechniques*, 7:328–336, 1994.
Drmanac et al., *Electrophoresis*, 13:566–573, 1992a.
Drmanac et al., *In The Second International Conference on Bioinformatics, Supercomputing, and Complex Genome Analysis*, 1992b.
Drmanac et al., *Identification of Transcribed Sequences*, New York: Plenum Press, 1994b.
Garey and Johnson, "*Computers and Intractability*," Freeman, 1979.
Grujic et al., *BioTechniques*, 17:291–294, 1994.
Hide et al., "Biological evaluation of $d^2$, and algorithm for high-performance sequence comparison," *Journal of Computational Biology*, 1(3):199–215, 1994.
Khan et al., *Nature Genetics*, 2:180–185, 1992.
Khrapko et al., *Journal of DNA Sequencing Mapping*, 1:375, 1991.
Lennon and Lehrach, "Hybridization analyses of arrayed cDNA libraries," *Trends in Genetics*, 7(10):314–317, 1991.
Li and Vitanyi, "An Introduction to Kolmogorov Complexity and its Applications," Springer Verlag, 1993.
Matsubara and Okubo, *Gene*, 135:265–274, 1993.
Meier-Ewert et al., *Nature*, 361:375–376, 1993.
Milner and Sutcliffe, *Nucleic Acids Research*, 11:5497–5520, 1983.
Milosavljevic, "Discovering sequence similarity by the algorithmic significance method. In L. Hunter, D. Searls, and J. Shavlik, editors, *Proceedings of the First International Conference on Intelligent Systems for Molecular Biology*, pages 284–291. AAAI Press, 1993.
Milosavljevic and Crkvenjakov, "Informatics for massive hybridization experiments. In *Abstract, Genome Sequencing and Analysis Conference V*, page 49—49, Hilton Head Island, S.C., 1993.
Pearson and Lipman, "Improved tools for biological sequence comparison," *Proceedings of the National Academy of Sciences U.S.A.*, 85:2444–2448, 1988.
Pevzner, "Statistical distance between texts and filtration methods in sequence comparison," *Computer Applications in Biosciences*, 8(2):121–127, 1992.
Pietrokovski et al., "Linguistic measure of taxonomic and functional relatedness of nucleotide sequences," *Journal* of biomolecules Structure and Dynamics, 7(6): 1251–1268, 1990.

Pizzi et al., "A simple method for global sequence comparison," *Nucleic Acids Research*, 20:131–136, 1991.

Pizzuti et al., "A transposon-like element in the deletion-prone region of the dystrophin gene," *Genomics*, 13:594–600, 1992.

Quentin, "Fast identification of repetitive elements in biological sequences," *Journal of Theoretical Biology*, 166:61–61, 1994.

Soares et al., *Proceedings of the National Academy of Science*, 91:9228–9232, 1994

Southern, PCT Patent Application, WO 89/10977

Southern et al., *Genomics*, 13:1008, 1992.

Storer, "*Data Compression: Methods and Theory.*," Computer Science Press, 1988.

Strezoska et al., *Proceedings of the National Academy of Sciences U.S.A.*, 88:10089, 1991.

Williams, "*Adaptive Data Compression*," Kluwer Academic Publishers, 1991.

---

What is claimed is:

1. A method for detecting sequence similarity between at least two nucleic acids, comprising the steps of:
   (a) identifying a plurality of putative subsequences from a first nucleic acid;
   (b) comparing said subsequences with at least a second nucleic acid sequence; and
   (c) aligning said subsequences using said second nucleic acid sequence in order to simultaneously maximize
      (i) matching between said subsequences and said second nucleic acid sequence and
      (ii) mutual overlap between said subsequences,
whereby said aligning predicts a subsequence that occurs within both said first and said second nucleic acids.

2. The method of claim 1, wherein said plurality of subsequences is identified by hybridization of said first nucleic acid with a set of oligonucleotide probes.

3. The method of claim 2, wherein said plurality of subsequences is identified by:
   (a) simultaneously contacting said first nucleic acid with an array of said set of oligonucleotide probes under conditions permitting hybridization of said oligonucleotide probes to substantially complementary regions within said first nucleic acid molecule; and
   (b) determining hybridization of individual oligonucleotide probes.

4. The method of claim 2, wherein said plurality of subsequences is identified by
   (a) simultaneously contacting said first nucleic acid, arrayed as a collection of nucleic acid fragments, with individual oligonucleotide probes of said set of oligonucleotide probes under conditions permitting hybridization of said set of oligonucleotide probes to substantially complementary regions within said arrayed collection of nucleic acid fragments; and
   (b) determining hybridizations of said oligonucleotide probes with said individual nucleic acids.

5. The method of claim 2, wherein said plurality of subsequences is identified by:

(a) contacting said first nucleic acid with an array of said set of oligonucleotide probes and a second set of oligonucleotide probes under conditions permitting hybridization of said oligonucleotide probes to regions within said first nucleic acid molecule that are substantially complementary to concatenations of said oligonucleotide probes; and (b) determining hybridization of said oligonucleotide probes.

6. The method of claim 1, wherein each of said putative subsequences is from six to twenty nucleotides.

7. The method of claim 1, wherein said second nucleic acid is predicted from an amino acid sequence or motif.

8. The method of claim 1, wherein said subsequences are used as a query to search a collection of nucleic acid sequences.

9. The method of claim 1, wherein said second nucleic acid is used as a query to search a collection of nucleic acid sequences, each nucleic acid sequence of said collection being represented by a list of subsequences.

10. The method of claim 1, wherein said aligning is a function of encoding length of the second nucleic acid.

11. The method of claim 1, wherein said aligning is a function of encoding length of said subsequences.

12. The method of claim 10, wherein said aligning is based on an estimate of mutual information between said second sequence and the said subsequences.

13. The method of claim 11, wherein said aligning is based on an estimate of mutual information between said second sequence and the said subsequences.

14. The method of claim 12, wherein the significance of said similarity is determined using basic or extended significance methods.

15. The method of claim 13, wherein the significance of said similarity is determined using basic or extended significance methods.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO:1:

GAAGTTGCGC ATGCACAAGT                                                        20

(2) INFORMATION FOR SEQ ID NO:2:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ix) FEATURE:
       (A) NAME/KEY: modified_base
       (B) LOCATION: one-of(4, 13)
       (D) OTHER INFORMATION: /mod_base= OTHER
           /note= "N = A, G, C, or T"

(xi) SEQUENCE DESCRIPTION: SEQ ID NO:2:

CCANAAGTTG CGNATGCAC                                                         19

(2) INFORMATION FOR SEQ ID NO:3:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ix) FEATURE:
       (A) NAME/KEY: modified_base
       (B) LOCATION: one-of(10, 13)
       (D) OTHER INFORMATION: /mod_base= OTHER
           /note= "N = A, G, C, or T"

(xi) SEQUENCE DESCRIPTION: SEQ ID NO:3:

GAAGTTGCGN ATNCACAAGT                                                        20

(2) INFORMATION FOR SEQ ID NO:4:

(i) SEQUENCE CHARACTERISTICS:
       (A) LENGTH: 10 base pairs
       (B) TYPE: nucleic acid
       (C) STRANDEDNESS: single
       (D) TOPOLOGY: linear

```
            (xi) SEQUENCE DESCRIPTION: SEQ ID NO:4:

AGTCAGTTTT                                                                    10

(2) INFORMATION FOR SEQ ID NO:5:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:5:

GATTACCGAT GAGCTAAT                                                           18

(2) INFORMATION FOR SEQ ID NO:6:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:6:

ATTACATGAG CATAAT                                                             16

(2) INFORMATION FOR SEQ ID NO:7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:7:

AGCTGAAGAG CAGCTAAA                                                           18

(2) INFORMATION FOR SEQ ID NO:8:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (xi) SEQUENCE DESCRIPTION: SEQ ID NO:8:

CATTTTTGTA C                                                                  11
```